(12) United States Patent
Ballandras et al.

(10) Patent No.: US 9,435,768 B2
(45) Date of Patent: Sep. 6, 2016

(54) METHOD OF INTERROGATING A SENSOR OF SURFACE ACOUSTIC WAVE TYPE

(75) Inventors: Sylvain Ballandras, Besancon (FR); Jean-Michel Friedt, Besancon (FR); Thibault Retornaz, L'Hôpital du Gros-Bois (FR)

(73) Assignee: SENSEOR, Mougins (FR)

( * ) Notice: Subject to any disclaimer, the term of this patent is extended or adjusted under 35 U.S.C. 154(b) by 825 days.

(21) Appl. No.: 13/588,501

(22) Filed: Aug. 17, 2012

(65) Prior Publication Data

US 2013/0211747 A1     Aug. 15, 2013

(30) Foreign Application Priority Data

Aug. 17, 2011   (FR) ...................... 11 57381

(51) Int. Cl.
*G01F 17/00*       (2006.01)
*G01N 29/22*       (2006.01)
*G06K 19/067*      (2006.01)

(52) U.S. Cl.
CPC ........... *G01N 29/22* (2013.01); *G06K 19/0675* (2013.01)

(58) Field of Classification Search
CPC .......................... G01N 29/22; G06K 19/0675
USPC ......................................................... 702/56
See application file for complete search history.

(56) References Cited

U.S. PATENT DOCUMENTS

| 2009/0121847 | A1* | 5/2009 | Solie et al. | 340/384.6 |
| 2009/0122830 | A1* | 5/2009 | Chomiki | 374/119 |
| 2010/0060429 | A1* | 3/2010 | Hines et al. | 340/10.1 |
| 2010/0117804 | A1 | 5/2010 | Malocha et al. | |
| 2010/0332157 | A1* | 12/2010 | Friedt | 702/54 |

FOREIGN PATENT DOCUMENTS

| EP | 1585056 A1 | 10/2005 |
| WO | 2004038637 A2 | 5/2004 |

\* cited by examiner

*Primary Examiner* — Mischita Henson
*Assistant Examiner* — Stephanie Bloss
(74) *Attorney, Agent, or Firm* — Baker Hostetler LLP (57) ABSTRACT

A method of interrogating sensors of SAW type, which allows notably the gathering of physical measurements of parameters carried out by SAW sensors, the method for gathering the measurement of an SAW sensor comprising a first step of generating and emitting an electromagnetic signal corresponding to the dilated time-reversal of a dilation coefficient k, of an impulse response signature which is characteristic of the SAW sensor, a second step of gathering a signal received as echo originating from the SAW sensor, a third step of determining a maximum of cross-correlation of the signal received as echo during the second step, the first step being applied with a set of values of the dilation coefficient k in a determined domain, the measurement of a physical parameter then being determined by the dilation coefficient k for which the power or the amplitude of the signal gathered as echo is a maximum.

8 Claims, 6 Drawing Sheets

METHOD OF INTERROGATING A SENSOR OF SURFACE ACOUSTIC WAVE TYPE

CROSS-REFERENCE TO RELATED APPLICATION

This application claims priority to foreign French patent application No. FR 1157381, filed on Aug. 17, 2011, the disclosure of which is incorporated by reference in its entirety.

FIELD OF THE INVENTION

The present invention relates to a method of interrogating a sensor of surface acoustic wave type. The present invention also relates to a device implementing such a method. It applies notably to the gathering of measurements carried out by sensors of surface acoustic wave type carrying out the measurement of at least one physical parameter, and by extension to their identification as well as any type of components of surface acoustic wave type.

BACKGROUND

Components of surface acoustic wave type, commonly denoted "SAW" components, according to the acronym corresponding to the English terminology "Surface Acoustic Wave", are present in numerous applications. For example, they can constitute devices for radiofrequency filtering, notably in telecommunication systems; they can also constitute radiofrequency identification devices or "RFID" according to the acronym denoting the English terminology "RadioFrequency IDentification", and form identification labels or "tags"; they can also constitute sensors of various physical parameters, such as temperature or pressure. SAW physical sensors can simultaneously ensure the functions of RFID tags and of physical sensors. Hereinafter, reference will be made to a "SAW sensor" to denote either an SAW physical sensor, an RFID tag or a SAW component ensuring these two functions.

SAW sensors present the advantage of being able to be interrogated remotely, but also of not requiring a power supply for such interrogation. Hereinafter, reference will be made to the interrogation of a SAW sensor, to denote equally the gathering of the information relating to its identification and/or to the measurement of a physical parameter. In a typical manner, SAW sensors may be made by depositing metallic patterns on a substrate composed of a piezoelectric material, for example quartz ($SiO_2$), lithium niobate ($LiNbO_3$) or lithium tantalate ($LiTaO_3$). The structures thus formed can in a typical manner comprise a resonator, for example consisting of interdigitated transducers, around which reflectors and electrodes are distributed. Radiofrequency electromagnetic signals can give rise to the generation of an elastic surface wave, e.g. Rayleigh wave, by the transducers, the elastic wave then propagates within the array of electrodes and reflectors, and the transducers then re-emit a radiofrequency signal which may be picked up by an antenna, and analysed by appropriate means. The configuration of these structures makes it possible to influence the propagation of the surface wave and to thus define typical response characteristics of the SAW sensors to determined signals, for example to a pulse of short duration modulated by a radiofrequency signal. A SAW sensor can thus be designed so as to offer its own inherent impulse response, defining its impulse response signature. An exemplary SAW sensor offering good performance, notably in terms of sensitivity to fabrication variations, is that of the reflective delay line, in which a transducer and several groups of reflectors or of electrodes are disposed on the surface of the piezoelectric substrate along the wave propagation axis. The distance between each group of reflectors and the transducer, multiplied by 2, the journey being two-way trip, divided by the phase speed of the wave, corresponds to the delay thus induced. Furthermore, physical parameters such as temperature or pressure may influence the phase speed and the propagation distance between reflector and transducer and therefore modify the delay defined above: more precise analysis of the temporal shape of the signal echoing for example a pulse, thus makes it possible to quantize a physical parameter, provided that the sensitivity coefficient of the delay/quantized value of the physical parameter characteristic is known. When the physical parameter measured is the temperature, this characteristic is for example represented by the temperature coefficient of the propagation delay of the surface waves. In a general way, reference will be made hereinafter to the term physical parameter coefficient of the propagation delay of the surface waves.

A wise choice of the architecture of the SAW sensor and notably of the materials used, for example jointly with the use of several sensors providing a differential measurement, can allow the selective measurement of a given physical parameter, for example temperature, in spite of the simultaneous influence of various physical parameters.

Efficient signal processing strategies have been developed for the purposes of the identification of a single SAW sensor and/or of the gathering of the measurement of the physical parameter, carried out by the latter. On the other hand, the identification and/or the gathering of measurement of a SAW sensor may turn out to be tricky, when several SAW sensors are close to an interrogation device. Indeed, the interrogation device then receives, for example as echo of an impulse signal, a signal which comprises the impulse response signals of the various SAW sensors, the latter possibly being entangled to the point of making it very difficult to discriminate the signals emanating from the various sensors.

Known solutions of the prior art implement complex methods of signal analysis making it possible to dissociate the signals. A known procedure is based on phase coding, and is described in the patent application published under the reference WO 2004/038637. However, such solutions exhibit the drawback of requiring relatively expensive calculation means. According to another known procedure, it is possible to manage code collision by orthogonality. However, according to this procedure, the standards relating to the frequency bands denoted ISM, according to the initials denoting the English terminology "Industrial, Scientific, Medical", that can be applied preferably to SAW sensors, are not complied with, and it is not permitted to emit signals beyond a certain quantity of energy in the spectral domain.

According to other prior art solutions which are in themselves known, the signatures of the various SAW sensors with which an interrogation device may be confronted, may be defined according to algorithms facilitating their dissociation by signal analysis means. However, such solutions exhibit the drawback of making it more complex to produce the SAW sensors, and of limiting the number of possible signatures according to a given production technology.

SUMMARY OF THE INVENTION

One aim of the present invention is to overcome at least the aforementioned drawbacks, by proposing a method for gathering a measurement of a physical parameter carried out by a SAW sensor, making it possible to retrieve the measurement in a robust manner, without requiring the implementation of particularly expensive and intensive, in terms of computation time, analysis processing.

An advantage of the invention is that it furthermore makes it possible to identify the SAW sensors from among a population, even numerous, of SAW sensors present in proximity to an interrogator device.

For this purpose, the subject of the invention is a method of interrogating a sensor of surface acoustic wave type carrying out a measurement of at least one physical parameter, comprising a first step of generating and emitting an electromagnetic signal corresponding to the time-reversal time-dilated by a dilation coefficient k, of an impulse response signature which is characteristic of the said acoustic sensor corresponding to the signal received from the sensor as echo to a determined signal of impulse type, a second step of gathering a signal received as echo of the signal emitted during the first step, a third step of determining the maximum value of the amplitude or of the power of the said signal received as echo during the second step, the said first step being applied in a new iteration with a dilation coefficient k increased or decreased by an amount of determined value, until the said maximum value attains a maximum value, the measurement of the said at least one physical parameter then being determined by the dilation coefficient k for which the maximum value is a maximum, and a coefficient of the said physical parameter of the propagation delay of the surface waves which is characteristic of the said acoustic sensor.

In one embodiment of the invention, the dilation coefficient k may be varied over the whole of the interval corresponding to the values of the physical parameter to be measured, the maximum value of the maximum value of the amplitude or of the power of the said signal received as echo being determined on the basis of all the values gathered over the interval of the values of the dilation coefficient k.

In one embodiment of the invention, the maximum value of the maximum value of the amplitude or of the power of the said signal received as echo may be determined for the dilation coefficient k corresponding to an iteration for which the rate of variation of the maximum value of the amplitude or of the power of the signal received as echo between the said iteration and the preceding iteration is of opposite sign to the rate of variation of the maximum value of the amplitude or of the power of the signal received as echo between the said preceding iteration and the iteration which precedes it.

In one embodiment of the invention, the interrogation method may be carried out for all the impulse response signatures of a set of known acoustic sensors, so that an identification of the acoustic sensors present can be carried out, an acoustic sensor being identified when the normalized maximum value of the amplitude or of the power of the signal received as echo during the second step is greater than a predetermined threshold value.

In one embodiment of the invention, the interrogation method can furthermore comprise a first prior step of gathering the signal in response to a determined emission signal, and a second prior step of analysing the gathered signal allowing the identification of one or more acoustic sensors, the said method then being carried out for the impulse response signatures of the known acoustic sensors thus identified during the said second prior step of analysing the gathered signal.

In one embodiment of the invention, the interrogation method can furthermore comprise a prior step of compiling a database of acoustic sensors, consisting in collecting for the set of known acoustic sensors able to be interrogated, and for a determined value of at least one physical parameter, the characteristic of the signal emitted by the said acoustic sensors in response to a determined signal of impulse type.

In one embodiment of the invention, the said predetermined threshold value may be a value greater than 70%.

The subject of the present invention is also an interrogation device for at least one sensor of surface acoustic wave type, characterized in that it implements a method according to any one of the embodiments described, the said interrogation device comprising an emission antenna linked to a radiofrequency signals shaping module linked to a radiofrequency signals synthesizer ensuring the implementation of the said first step, a reception antenna linked to an amplification and filtering module, implementing the said second step, the amplification and filtering module being linked to a radiofrequency analysis module implementing the said third step and determining the said measurement of the said at least one physical parameter.

The subject of the invention is also a device implementing a method according to any one of the embodiments of the invention forming the subject of the claims of the present patent application.

BRIEF DESCRIPTION OF THE DRAWINGS

Other characteristics and advantages of the invention will become apparent on reading the following description, given by way of example, and in conjunction with the appended drawings which represent.

DETAILED DESCRIPTION

According to the present invention, it is proposed to use the principle of time-reversal for the purposes of interrogating SAW sensors. The present invention is based on utilizing a property of elastic-wave transducers, carrying out naturally a convolution product between their transfer function and the signal of the incident wave. Hence, the signal received as echo of an emission of a signal corresponding to the time-reversal of the impulse response of an elastic-wave transducer, corresponds to a function for the cross-correlation between the impulse response of the transducer, and an impulse response of the latter, known in advance and for example stored.

The principle of time-reversal, known per se from the prior art, is the basis of various known techniques, making it possible notably to locate dense structures, such as for example renal calculi, in a biological medium, and to focus energy thereon so as to destroy them. Time-reversal is also utilized in the field of acoustic imaging, with the aim of improving the contrast, that is to say the signal-to-noise ratio, of echographic images, and more prosaically to precisely determine precise targets in strong-scattering media, in which a random distribution of acoustic obstacles exists. Techniques based on the principle of time-reversal also apply to electromagnetic waves, and make it possible notably to carry out focusings so as to transmit radiofrequency messages between several systems, typically equipped with antennas, while guaranteeing a gain in signal-to-noise ratio with respect to the conventional procedures of detection/direct transmission, as well as high selectivity, in the sense that they make it possible for a given antenna to pick up exclusively the signals intended for it, whilst even a neighbouring antenna does not pick up these same signals.

In a typical manner, a method of time-reversal comprises a step consisting in gathering the echo produced by a physical system in consequence of an initial impulse stimulation, followed by a step consisting in re-emitting the gathered echo, after having reversed it in time. In consequence of the latter emission, the system then re-emits the initial pulse. The principle of time-reversal relies on the invariance of the wave propagation equation under time-inversion.

According to the present invention, it is proposed to emit towards a system, an electromagnetic signal corresponding to the time-reversal of the impulse response signature which is characteristic of a SAW sensor to be interrogated. The impulse response signature which is characteristic of a SAW sensor is the signal received as echo of a signal of impulse type, for example an electromagnetic signal of high frequency of large amplitude and emitted over a very short duration, when it is emitted towards the isolated SAW sensor, the environmental physical parameters of the SAW sensor being fixed arbitrarily. An alternative for the identification of the impulse response of a transducer is frequency scanning so as to identify the response ($S_{11}$) of the transducer over a wide band and then to perform the inverse Fourier transform to obtain the impulse response in the time domain.

In this way, an electromagnetic signal is re-emitted by the system—and notably by the SAW sensor to be interrogated—as echo of the time-reversed signal, and the echo signal may be gathered and analysed. Now, when the SAW sensor to be interrogated is sensitive to a determined parameter, that is to say when the SAW sensor carries out the measurement of this physical parameter, the time-dilation of the signal representative of its impulse response varies as a function of the quantized value of the physical parameter.

Figure 5:
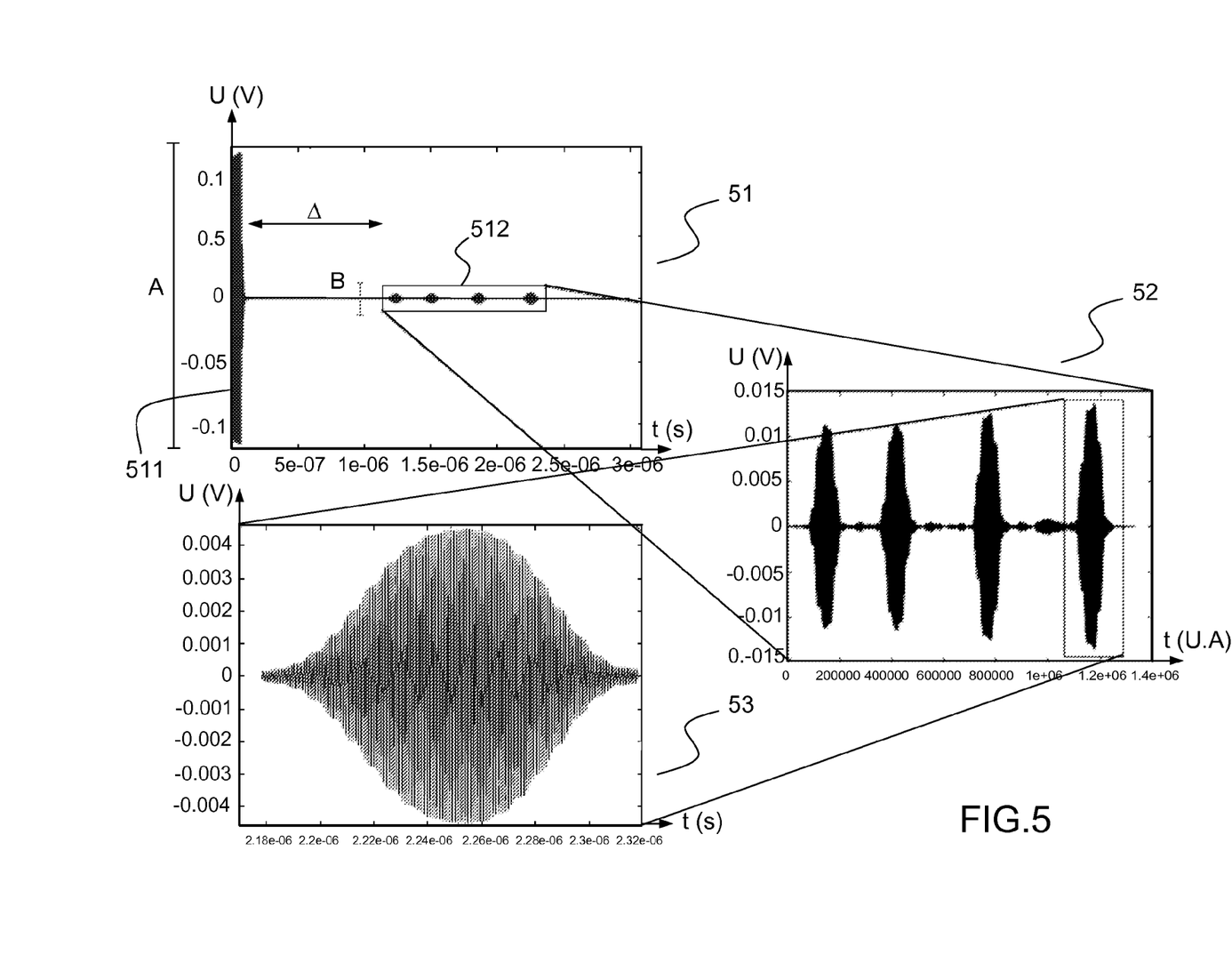
FIG. 5, curves illustrating the response of a delay line, to a radiofrequency signal of impulse type.
Figure 6:
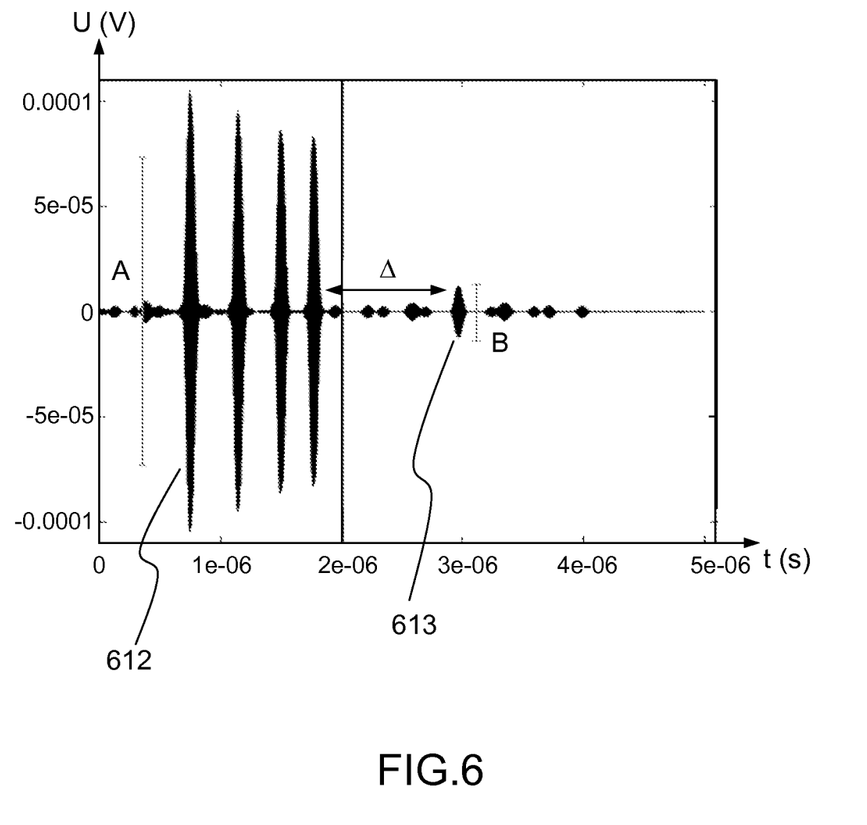
FIG. 6, curves illustrating the response of a delay line, to a radiofrequency signal corresponding to the time-reversal of the impulse response signal of the delay line, according to an exemplary embodiment of the invention.

Examples of curves representative of signals emitted and gathered as echo, in examples where the SAW sensor considered is a delay line, are illustrated by FIGS. 5 and 6 described briefly hereinafter.

Thus, the closer to the current quantized value of the physical parameter to which the SAW sensor is subjected is the time-dilation exhibited by the time-reversed signal, the more strongly correlated with the signal of initial impulse type is the signal received as echo of the system subjected to the variations of the physical parameter considered. Stated otherwise, the closer the dilating factor k to the scaling effect of the physical quantity under investigation as applied to the time reversed impulse response, the better the correlation between the emitted signal and the transfer function of the sensor as observed through the magnitude of the returned signal.

A fundamental principle of the present invention consists in varying the time-dilation of the time-reversed signal emitted, by scanning values of a time-dilation coefficient in a span of values corresponding to a span of the quantized values of the physical parameter measured by the SAW sensor, and in analysing the maximum value of the amplitude or of the power of the signal received as echo, corresponding to the rate of cross-correlation between the impulse response of the sensor and the signal of the latter's initially determined impulse response. Thus when the cross-correlation rate is a maximum, the value of the corresponding time-dilation coefficient can allow a determination of the quantized value of the physical parameter measured by the SAW sensor, provided that the characterization of the latter, in terms of coefficient of the said physical parameter of the propagation delay of the surface waves, is known.

Thus, it is possible to carry out the method forming the subject of the present invention, for the interrogation of an SAW sensor whose characteristics are known in advance, and whose sensitivity to the phenomenon to be measured is manifested mainly by a time-dilation of its impulse response.

Advantageously, it is possible to carry out the method for the interrogation of a plurality of known SAW sensors whose presence in the environment of an interrogator device is known in advance, by emitting the time-reversed signals corresponding respectively to all the impulse response signatures characteristic of the various SAW sensors to be interrogated: for example, it is possible to interrogate via a unique interrogator device, several known SAW sensors disposed in a vehicle, some of which measure the local temperature at critical points, and others of which measure tyre pressures, etc.

Advantageously again, it is possible to carry out a method in which a plurality of time-reversed signals corresponding respectively to all the impulse response signatures characteristic of a set of various SAW sensors potentially present in proximity to an interrogator device, without the presence or the absence of these SAW sensors being known in advance. In this way, it is possible to undertake the identification of the SAW sensors present, as well as the gathering of the measurement of physical parameters that they carry out if appropriate. For example, it is possible to carry out such a method "in a loop", for the detection, the identification and the gathering of measurements of SAW sensors within the range of an interrogator device, the time-reversed signals corresponding to all the SAW sensors potentially present being emitted in turn, the scanning of the time-dilation coefficients being carried out for each of them, the presence of an SAW sensor being able for example to be asserted if the cross-correlation rate, that is to say the maximum value of the amplitude or of the power of the signal received as echo, exceeds a threshold value. Such an embodiment can for example apply to the dynamic management of a stock of merchandise, wherein it may be necessary to identify the merchandise disposed on a conveyor belt, and passing in proximity to an interrogator device, the merchandise being equipped with RFID tags and potentially with SAW physical sensors. The various embodiments mentioned hereinabove are described in detail hereinafter, with reference to FIGS. 1 to 6.

Figure 1:
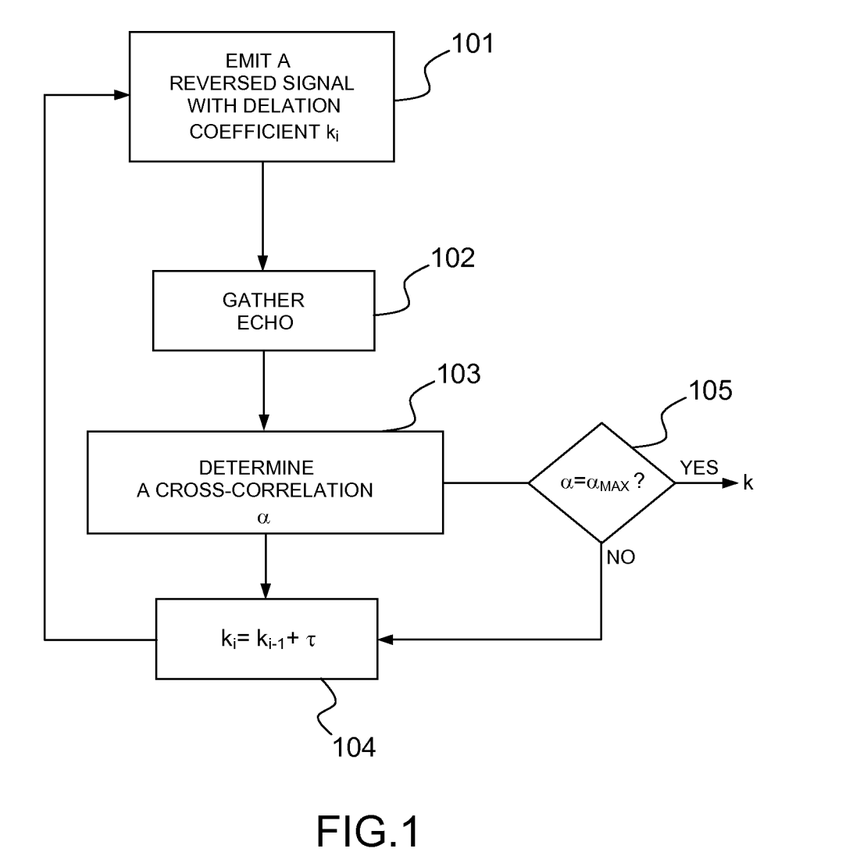
FIG. 1, a logic diagram illustrating a method of interrogating an SAW sensor carrying out the measurement of a physical parameter, according to an exemplary embodiment of the invention.

FIG. 1 presents a logic diagram illustrating a method of interrogating an SAW sensor carrying out the measurement of a physical parameter, according to an exemplary embodiment of the invention.

According to the nonlimiting exemplary embodiment of the present invention, illustrated by FIG. 1, a method for gathering the measurement carried out by a SAW sensor, for example disposed in a system in proximity to an interrogation device, can comprise a first step 101 consisting in emitting an electromagnetic signal corresponding to the time-reversal of the impulse response signature of the SAW sensor to be interrogated, followed by a second step 102 consisting in gathering the signal received as echo. In a first iteration, the electromagnetic signal may be assigned an initial time-dilation coefficient $k_0$. The initial time-dilation coefficient $k_0$ may be for example that which defines an impulse response signature of the SAW sensor when the value of the physical parameter is the minimum quantized value in the expected measurement span.

The signal thus gathered can then be analysed during a third step 103, during which a maximum value is determined. This maximum value corresponds to the maximum value of a function for the cross-correlation between the signal s' received as echo during the second step 102, and the initial signal s of impulse type that produced the impulse response signature of the SAW sensor. This maximum value thus corresponds to the cross-correlation rate. Storage of the aforementioned maximum value can then be carried out, and a step of incrementing the time-dilation coefficient 104 can increase the time-dilation coefficient $k_0$ by an amount $\tau$ of determined value, positive or negative, depending notably on the choice of the initial value $k_0$ of the time-dilation coefficient, the time-dilation coefficient then taking an incremented value $k_1$.

The method can then begin again in a second iteration, resuming at the first step 101, during which an electromagnetic signal is then emitted, corresponding to the impulse response signature of the SAW sensor, assigned a time-dilation coefficient $k_1$, etc., the steps of the method being conducted in a loop, for example so that the time-dilation coefficient k takes all the values $k_i$ enabling total coverage of the interval of quantized values of the physical parameter the measurement of which is carried out by the SAW sensor.

A step of determining the maximum value 105 of the maximum value of the amplitude or of the power of the signal received as echo, aforementioned, can then make it possible to determine the value of the time-dilation coefficient $k_i$ for which the said maximum value is a maximum.

Advantageously, it may not be necessary to vary the values of the time-dilation coefficient $k_i$ in such a way that the latter enables total coverage of the interval of values to be measured, and the step of determining the maximum value 105 of the said maximum value of the amplitude or of the power of the signal received as echo, aforementioned, can for example compare a value of the maximum value determined in an i-th current iteration, with the maximum value determined in the (i−1)-th preceding iteration, and a loop exit may be carried out, for example if the variation upwards or downwards of the maximum value from one iteration to the next reverses, or stated otherwise if the coefficient of variation of the maximum value has changed sign between the (i−2)-th iteration and the (i−1)-th iteration and between the (i−1)-th iteration and the i-th iteration.

Whatever procedure is implemented to determine the maximum of correlation, that is to say of the maximum value of the amplitude or of the power of the signal received as echo, the value of the time-dilation coefficient corresponding thereto makes it possible to determine the quantized value of the physical parameter measured by the SAW sensor if appropriate. This value may be determined using the coefficient of the physical parameter of the propagation delay of the surface waves which is characteristic of the SAW sensor considered.

Figure 2:
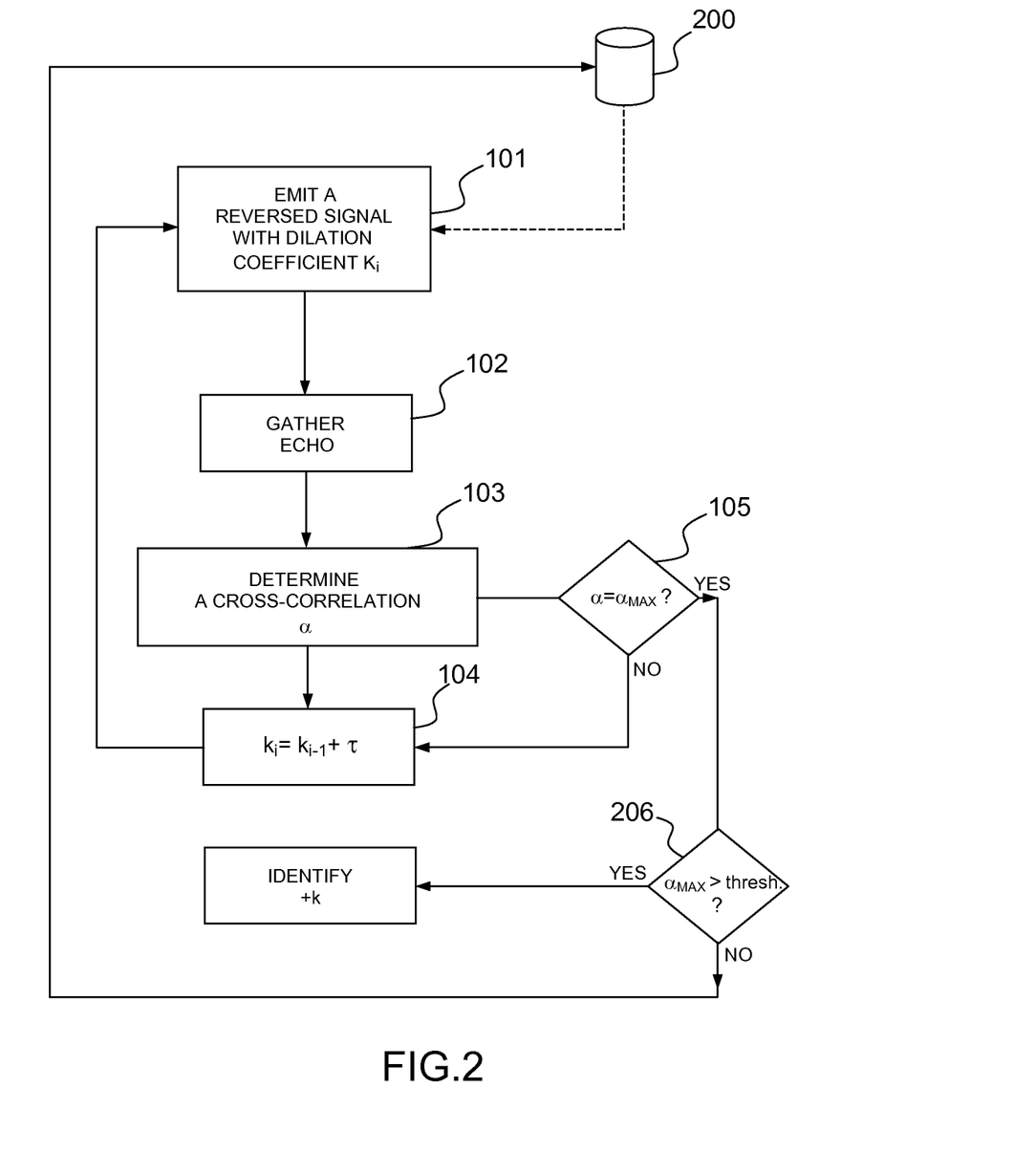
FIG. 2, a logic diagram illustrating an interrogation method such as illustrated by FIG. 1, furthermore allowing the identification of SAW sensors present and the gathering of the measurement of the physical parameters carried out by the latter, according to an exemplary embodiment of the invention.

Advantageously, it is possible to undertake the identification of the SAW sensors present, as well as the gathering of the measurement of the physical parameter that they carry out if appropriate. FIG. 2 described in detail hereinafter presents a nonlimiting example of this in the present invention.

FIG. 2 presents a logic diagram illustrating an interrogation method such as illustrated by FIG. 1, furthermore allowing the identification of SAW sensors present and the gathering of the measurement of the physical parameters carried out by the latter, according to an exemplary embodiment of the invention.

The method described in FIG. 2 also comprises the first, second and third steps 101, 102, 103 described previously with reference to FIG. 1, as well as the step of incrementing the time-dilation coefficient 104 and the step of determining the maximum value 105 of the maximum value of the amplitude or of the power of the signal received as echo.

The method described in FIG. 2 can for example be carried out for all the electromagnetic signals (dilated and time-reversed) corresponding to the impulse response signatures of a set of SAW sensors to be interrogated included in a database 200.

A step of comparing a normalized cross-correlation rate 206 may be added, making it possible to calculate a normalized cross-correlation rate, for example on the basis of the maximum value of the amplitude or of the power of the signal received as echo, aforementioned, divided by the possible maximum value of the latter, and to compare the normalized cross-correlation rate with a predetermined threshold value. The predetermined threshold value can for example be chosen greater than or equal to 70%.

If the normalized cross-correlation rate is for example greater than or equal to the predetermined threshold value, then it may be considered that the corresponding SAW sensor is present, and if the latter carries out a measurement of a physical parameter, said measurement may be determined on the basis of the value of the time-dilation coefficient making it possible to maximize the cross-correlation rate, as described previously, using the coefficient of the physical parameter of the propagation delay of the surface waves which is characteristic of the SAW sensor considered, this datum possibly also being included in the database.

Stated otherwise, the database 200 comprises, for all the SAW sensors with which an interrogator device may be confronted, their impulse response signatures, as well as the information relating to their respective characteristic coefficients of the physical parameter of the propagation delay of the surface waves. The interrogation method according to one of the exemplary embodiments described can furthermore comprise a prior step aimed at constructing the database 200, as is described hereinafter with reference to a nonlimiting example illustrated by FIG. 3.

In one embodiment of the invention, it is possible to supplement the interrogation method with a first prior step of gathering the signal received as echo, in response to a determined emission signal for example of impulse type, and a second prior step of analysing the gathered signal, for example according to a technique known per se of interrogation of SAW sensors. In this way, it may be possible to carry out a pre-identification of one or more acoustic sensors, and thereafter to carry out the method, as described previously, only for the impulse response signatures of the known acoustic sensors thus identified, during the second prior step of analysing the gathered signal.

Figure 3:
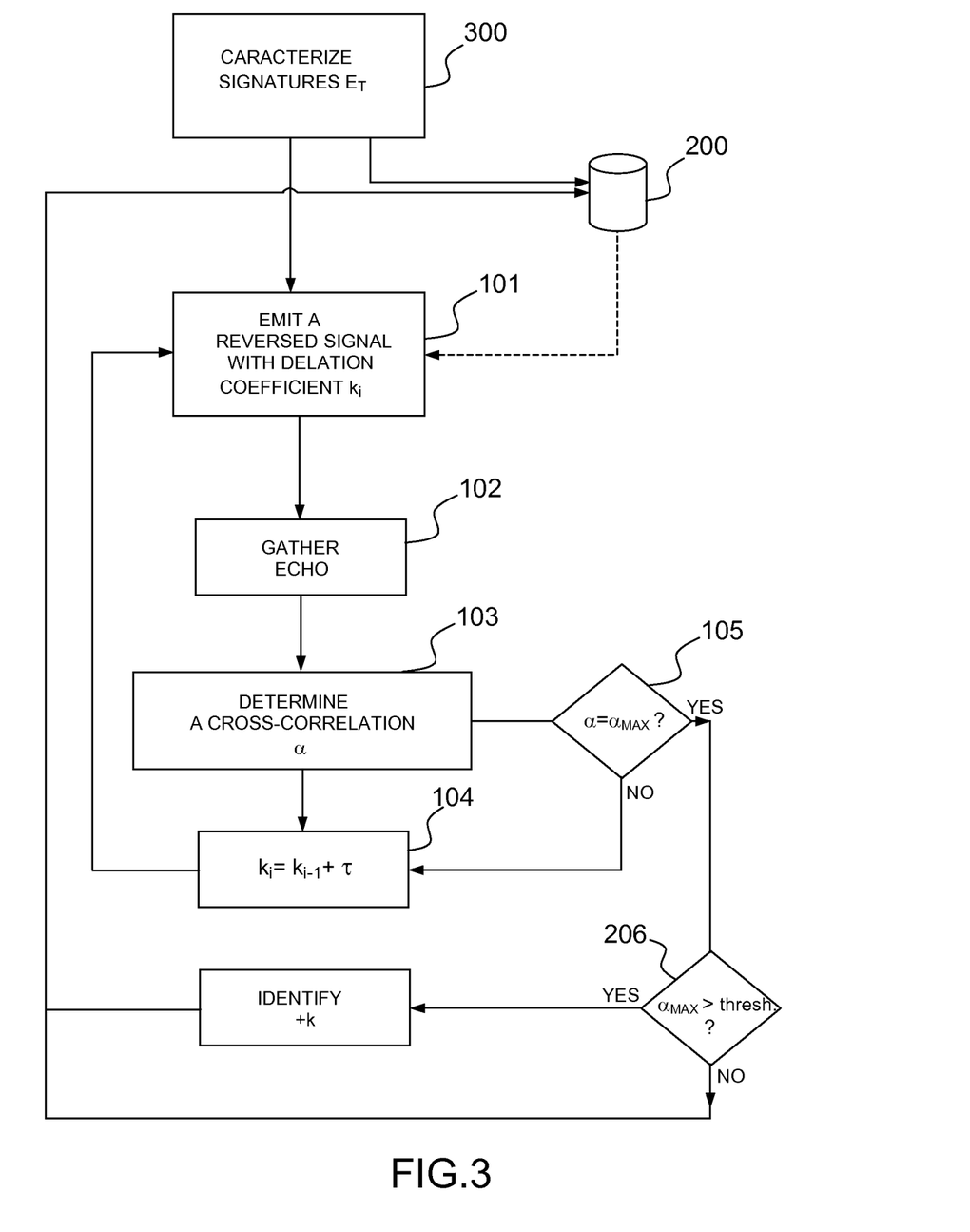
FIG. 3, a logic diagram illustrating a method such as described by FIG. 2, furthermore comprising a prior step of compiling a database of SAW sensors, according to an exemplary embodiment of the invention.

FIG. 3 presents a logic diagram illustrating a method such as described by FIG. 2, furthermore comprising a prior step of compiling a database of SAW sensors, according to an exemplary embodiment of the invention. Prior knowledge of the characteristics of the interrogatable SAW sensors is indeed necessary.

The method illustrated by FIG. 3 differs from the method illustrated by FIG. 2 and described hereinabove in that it exhibits a prior step 300 of characterizing the potentially interrogatable SAW sensors. The prior step 300 can consist in emitting towards each of the interrogatable SAW sensors taken in isolation, a predetermined signal, for example of impulse type, and gathering and storing the signal $E_T$ received as echo. The prior step 300 may be carried out for a given value of the physical parameter measured by the SAW sensor, for example for a given temperature T. The gathered signals can for example be sampled and the corresponding data stored in the aforementioned database 200.

It is also possible to characterize a SAW sensor other than by impulse response: for example by inverse Fourier transform of its spectral response, or by any other known means.

Figure 4:
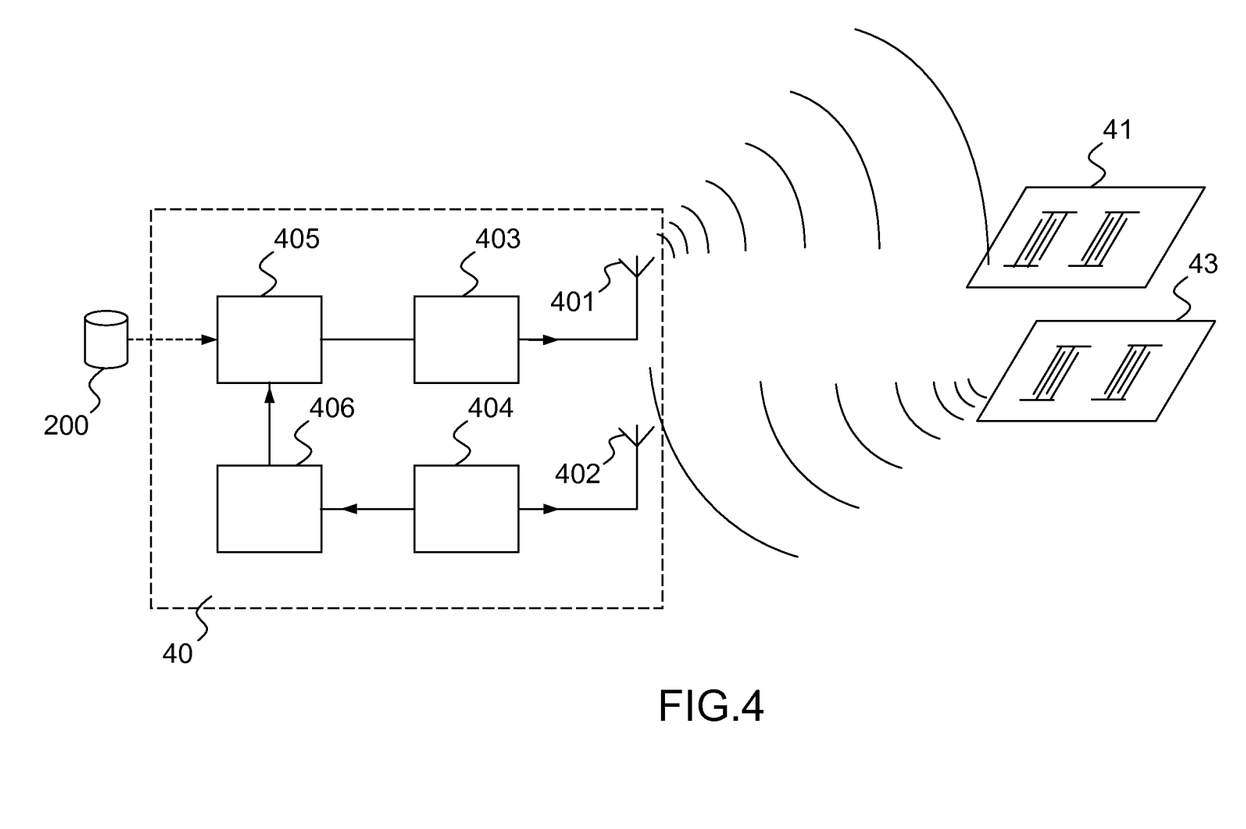
FIG. 4, a diagram illustrating in a schematic manner, an exemplary device implementing a method according to one of the embodiments of the present invention.

FIG. 4 presents a diagram illustrating in a schematic manner an exemplary device implementing a method according to one of the embodiments of the present invention.

FIG. 4 presents an interrogator device 40 configured to emit radiofrequency signals destined for SAW sensors 41, 43, two of which are represented in the figure. The interrogator device 40 comprises an emission antenna 401 and a reception antenna 402, the emission and reception antennas 401, 402 possibly being for example co-located.

The emission antenna 401 is linked to a radiofrequency signals shaping module 403 ensuring notably frequency transposition if necessary, and the amplification of the signals generated by a radiofrequency synthesizer 405. The radiofrequency synthesizer 405, which allows the synthesis of the previously described time-reversed signals, is linked for example to the database 200, the database 200 possibly being integrated physically into the radiofrequency synthesizer 405. These various elements thus allow the implementation of the first step of the methods described previously with reference to FIGS. 1 to 3.

The signals picked up by the reception antenna 402 can drive an amplification and filtering module 404. The amplification and filtering module 404 may be linked to a radiofrequency analysis module 406. The reception antenna 402 and the amplification and filtering module 404 allow notably the implementation of the second step 102 of gathering signals as echo, described previously with reference to FIGS. 1 to 3, of the third step of determining an cross-correlation rate 103, the step of incrementing the time-dilation coefficient 104 and the step of determining the maximum value 105 of the cross-correlation rate, as well as the step, described previously with reference to FIGS. 2 and 3, of comparing the normalized cross-correlation rate 206, and the prior step 300 of characterizing the interrogatable SAW sensors. The various calculations necessary for these steps can for example be implemented in the radiofrequency analysis module 406, or else in an external calculation module connected to the radiofrequency analysis module 406, not represented in the figure. It is recalled here, as was mentioned previously, that the cross-correlation rate arises directly from the maximum value of the amplitude or of the power of the signal received as echo of a sensor, upon the emission of a time-reversal of a signal characteristic of its impulse response: consequently the present invention does not involve any calculation of an cross-correlation function, the cross-correlation being carried out naturally by the SAW sensor, which by construction carries out a convolution product of the incident signal with its transfer function.

FIG. 5 presents curves illustrating the response of a delay line to a radiofrequency signal of impulse type.

FIG. 5 presents a first graphical representation 51 of the voltage across the terminals of the delay line forming an SAW sensor in the example considered, as a function of time. A first high-frequency pulse 511, of a frequency of the order of 2.4 GHz typical of an ISM band according to the initials denoting the term "Industrial, Scientific and Medical" of large amplitude A and of short duration corresponds to an emitted signal of impulse type. A series of four pulses 512 of lesser amplitude starts after a lag A subsequent to the high-frequency pulse, whose mean amplitude value is denoted B, corresponds to the impulse response signature of the delay line. In the example illustrated by the figure, the ratio between the amplitudes A and B is of the order of 20, and the lag A is of the order of a microsecond.

A second graphical representation 52 presents an enlargement of the series of four pulses 512, and a third graphical representation presents an enlargement of the fourth pulse of the series of four pulses 512.

FIG. 6 presents curves illustrating the response of a delay line to a radiofrequency signal corresponding to the time-reversal of the delay line impulse response signal, according to an exemplary embodiment of the invention.

In the example illustrated by FIG. 6, a first series of four pulses 612 corresponds to the time-reversal time-dilated by a dilation coefficient equal to 1, of the delay line impulse response signal, that is to say of the signal depicted by the series of four pulses 512, such as is described previously with reference to FIG. 5.

A second series of pulses appears approximately 1 μs after the end of the first series of four pulses 612, that is to say after a lag substantially equal to the aforementioned lag Δ, and corresponds to the typical response of a system comprising the delay line. The second series of pulses is centred on a main lobe 613 corresponding to an cross-correlation spike, around which sidelobes are visible.

In the example illustrated by the figure, the ratio between the mean amplitude of the first series of four pulses 612, and the amplitude of the main lobe 613, is of the order of 5.

It should be noted that the present invention can apply to the interrogation of devices composed of transducers and of reflectors forming a reflective delay line, as well as to any device combining combs that are active electrically or operating only as wave reflector, liable to exhibit an impulse response differentiable from a population of sensors/devices according to this same definition.

More generally, the present invention can apply to any elastic-wave device exhibiting an impulse response.

The present invention can advantageously be implemented for remote interrogation, but can also be applicable to devices connected in parallel and interrogated by wire, and therefore apply to all piezoelectric substrates customarily used for sensors and more generally elastic-wave devices.

The invention claimed is:

1. A method of interrogating an acoustic sensor of surface acoustic wave type carrying out a measurement of at least one physical parameter, said method comprising:
   a first step of generating and emitting an electromagnetic signal related to an impulse response signature, the electromagnetic signal being a time-reversal and a time-dilation, by a dilation coefficient k, of the impulse response signature, said impulse response signature being associated with an echo to a determined impulse signal, the impulse response signature being characteristic of said acoustic sensor, wherein the time-reversal includes mirroring the impulse response signature about a time axis and the time-dilation includes a scaling along a time axis of the impulse response signature based upon the dilation coefficient k,
   a second step of gathering a signal received as the echo of the electromagnetic signal emitted during the first step,
   a third step of determining the maximum value of the amplitude or of the power of the said signal received as echo during the second step,
   said first step being applied in a new iteration with a dilation coefficient k increased or decreased by an amount of determined value, until said maximum value attains a maximum value,
the measurement of said at least one physical parameter then being determined by the dilation coefficient k for which the maximum value is a maximum, and a coefficient of said physical parameter of the propagation delay of the surface waves which is characteristic of said acoustic sensor.

2. The method of claim 1, wherein the dilation coefficient k is varied over the whole of the interval corresponding to the values of the physical parameter to be measured, the maximum value as a function of the dilation coefficient k of the maximum value of the amplitude or of the power of said signal received as echo being determined on the basis of all the values gathered over the interval of the values of the dilation coefficient k.

3. The method of claim 1, wherein the maximum value of the maximum value of the amplitude or of the power of the said signal received as echo is determined for the dilation coefficient k corresponding to an iteration for which the rate of variation of the maximum value of the amplitude or of the power of the signal received as echo between said iteration and the preceding iteration is of opposite sign to the rate of variation of the maximum value of the amplitude or of the power of the signal received as echo between said preceding iteration and the iteration which precedes it.

4. The method of claim 1, carried out for all the impulse response signatures of a set of known acoustic sensors, so that an identification of the acoustic sensors present can be carried out, an acoustic sensor being identified when the normalized maximum value of the amplitude or of the power of the signal received as echo during the second step is greater than a predetermined threshold value.

5. The method of claim 4, further comprising a first prior step of gathering the signal in response to a determined emission signal, and a second prior step of analysing the gathered signal allowing the identification of one or more acoustic sensors, said method then being carried out for the impulse response signatures of the known acoustic sensors thus identified during said second prior step of analysing the gathered signal.

6. The method of claim 4, in which said predetermined threshold value is a value greater than 70%.

7. The method of claim 1, further comprising a prior step of compiling a database of acoustic sensors, consisting in collecting for the set of known acoustic sensors able to be interrogated, and for a determined value of at least one physical parameter, the characteristic of the signal emitted by the said acoustic sensors in response to a determined signal of impulse type.

8. An interrogation device for at least one sensor of surface acoustic wave type, implementing a method according to claim 1, the interrogation device comprising:
   an emission antenna linked to a radiofrequency signal shaping module linked to a radiofrequency signal synthesizer ensuring the implementation of the first step,
   a reception antenna linked to an amplification and filtering module, implementing the second step, increasing or decreasing the dilation coefficient by the amount of determined value until the maximum value of the amplitude or of the power attains a maximum value for an optimal value of the dilation coefficient k, the amplification and filtering module being linked to a radiofrequency analysis module implementing the third step and determining the measurement of the at least one physical parameter, based on the dilation coefficient k with which said maximum value is maximum, and a coefficient of the physical parameter of the propagation delay of the surface waves which is characteristic of the acoustic sensor.

* * * * *